(12) United States Patent
Wittmeier

(10) Patent No.: US 9,613,421 B2
(45) Date of Patent: Apr. 4, 2017

(54) OPTICAL TRACKING

(71) Applicant: CureFab Technologies GmbH, Munich (DE)

(72) Inventor: Sebastian Wittmeier, Munich (DE)

(73) Assignee: CUREFAB TECHNOLOGIES GMBH, Munich (DE)

( * ) Notice: Subject to any disclaimer, the term of this patent is extended or adjusted under 35 U.S.C. 154(b) by 0 days.

(21) Appl. No.: 14/463,212

(22) Filed: Aug. 19, 2014

(65) Prior Publication Data

US 2016/0171702 A1  Jun. 16, 2016

(30) Foreign Application Priority Data

Aug. 20, 2013 (EP) .................................. 13180985

(51) Int. Cl.
| | | |
|---|---|---|
| *G06T 7/00* | (2006.01) | |
| *G01S 11/12* | (2006.01) | |
| *A61B 8/00* | (2006.01) | |
| *G06T 7/20* | (2017.01) | |

(52) U.S. Cl.
CPC .......... *G06T 7/0044* (2013.01); *A61B 8/4245* (2013.01); *A61B 8/4254* (2013.01); *G01S 11/12* (2013.01); *G06T 7/0042* (2013.01); *G06T 7/2033* (2013.01); *G06T 7/2086* (2013.01); *G06T 2207/10021* (2013.01); *G06T 2207/30204* (2013.01)

(58) Field of Classification Search
CPC ..... G06T 7/004; G06T 7/0042; G06T 7/0044; G06T 7/2033; G06T 7/2086; G06T 2207/10021; G06T 2207/30204; A61B 8/4245; A61B 8/4254; G01S 11/12
See application file for complete search history.

(56) References Cited

U.S. PATENT DOCUMENTS

| | | | | |
|---|---|---|---|---|
| 6,491,632 | B1 * | 12/2002 | Taylor ...................... | A61B 8/08 128/916 |
| 6,925,339 | B2 * | 8/2005 | Grimm .................. | A61B 34/20 606/130 |
| 7,029,477 | B2 * | 4/2006 | Grimm ................ | A61B 17/157 606/88 |
| 7,580,027 | B2 * | 8/2009 | Satoh ..................... | G01S 5/163 345/156 |
| 7,599,789 | B2 * | 10/2009 | Leonard ............... | G01C 21/005 382/103 |
| 7,677,078 | B2 * | 3/2010 | Sauer ....................... | A61B 5/06 73/1.82 |
| 2004/0100557 | A1 * | 5/2004 | Roberts ................. | G01S 3/7864 348/169 |

(Continued)

OTHER PUBLICATIONS

Foxlin E et al. "FlightTracker: A Novel Optical/Inertial Tracker for Cockpit Enhanced Vision", Proceedings of the Third IEEE and ACM International Symposium on Mixed and Augmented Reality, Nov. 2-5, Arlington, VA, IEEE, Piscataway, NJ, USA, Nov. 2, 2004 (Nov. 2, 2004), pp. 212-221, XP010769700.

(Continued)

*Primary Examiner* — Manav Seth
(74) *Attorney, Agent, or Firm* — Norris McLaughlin & Marcus P.A.

(57) ABSTRACT

The present invention relates to a method for determining the pose of an object, preferably of a medical device.

16 Claims, 6 Drawing Sheets

(56) References Cited

U.S. PATENT DOCUMENTS

| | | | |
|---|---|---|---|
| 2007/0092161 A1* | 4/2007 | Aratani | G06T 7/0042 |
| | | | 382/286 |
| 2009/0306509 A1 | 12/2009 | Pedersen et al. | |
| 2013/0135463 A1* | 5/2013 | Aratani | H04N 7/18 |
| | | | 348/135 |
| 2013/0156264 A1 | 6/2013 | Maartensson | |
| 2013/0162785 A1 | 6/2013 | Michot et al. | |
| 2013/0237811 A1* | 9/2013 | Mihailescu | A61B 5/064 |
| | | | 600/424 |
| 2013/0251204 A1* | 9/2013 | Pulsipher | G06K 9/00369 |
| | | | 382/103 |
| 2015/0182191 A1* | 7/2015 | Caluser | A61B 5/4312 |
| | | | 600/440 |
| 2015/0379718 A1* | 12/2015 | Schubert | G06T 7/0042 |
| | | | 382/131 |
| 2016/0022173 A1* | 1/2016 | Schubert | G06T 7/0042 |
| | | | 600/587 |
| 2016/0113728 A1* | 4/2016 | Piron | A61B 17/3421 |
| | | | 606/130 |

OTHER PUBLICATIONS

Yanagihara Y et al: "A spatial postion tracker for work-site teachings of sensor-enhanced robotic systems", Robot and Human Communication, 1997. RO-MAN '97. Proceedings., 6th IEEE International Workship on Sendai, Japan Sep. 29-Oct. 1, 1997, New York, NY, USA, IEEE, US, Sep. 29, 1997 (Sep. 29, 1997), pp. 182-186, XP010263196.

* cited by examiner

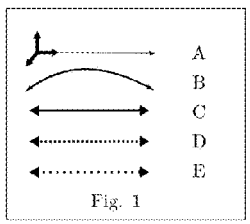
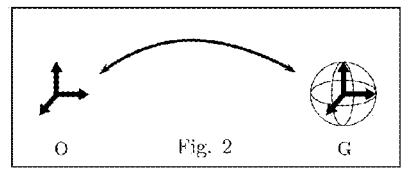
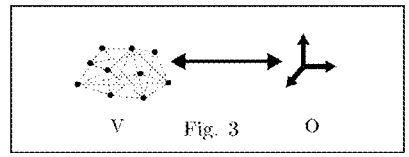
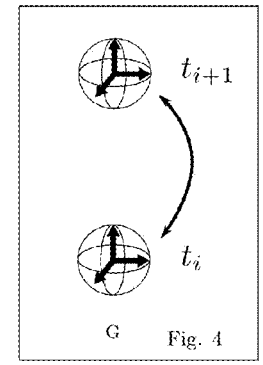
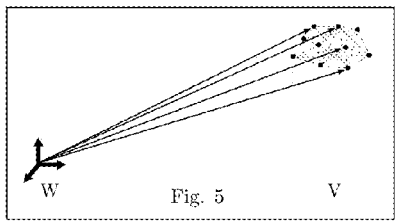
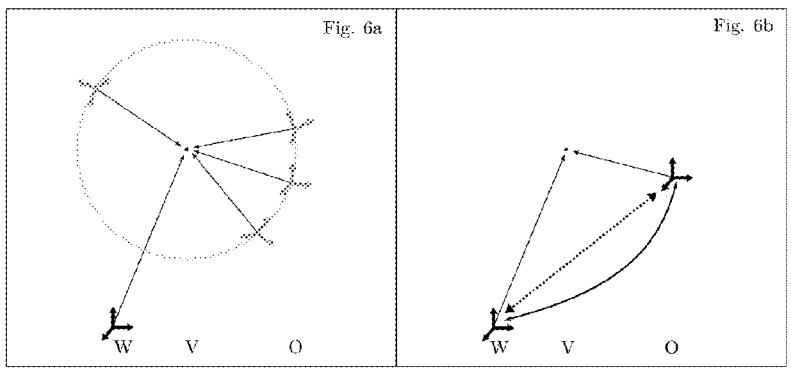
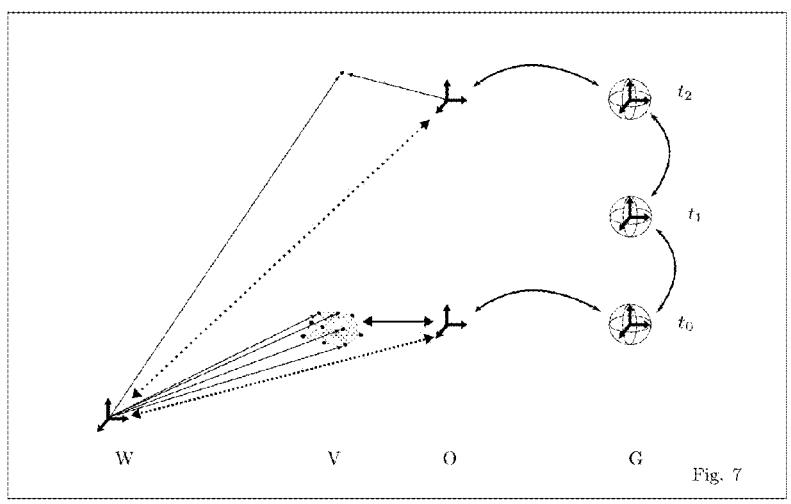

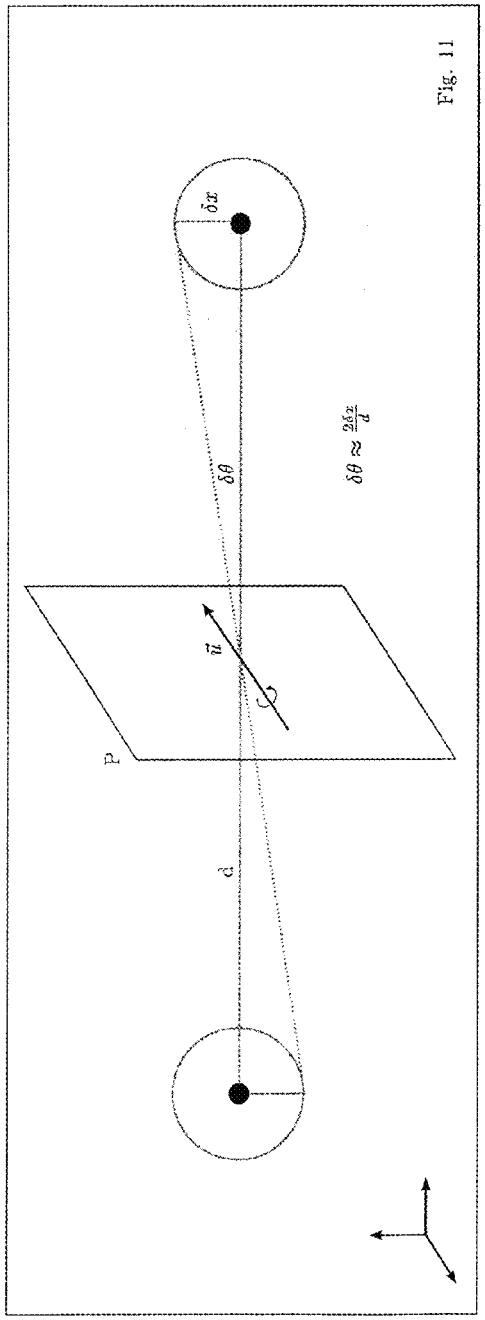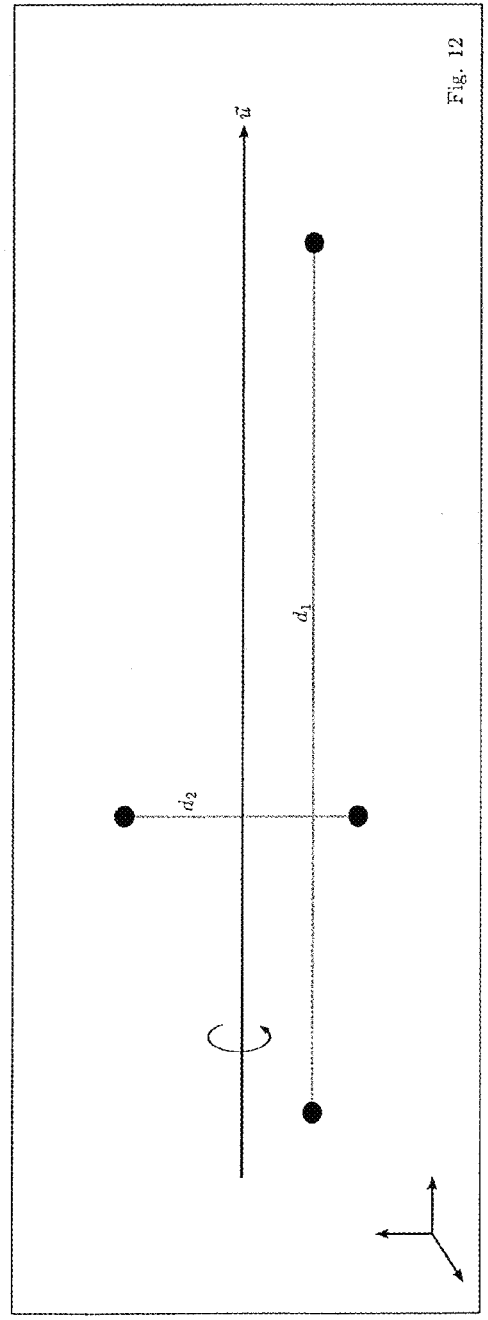

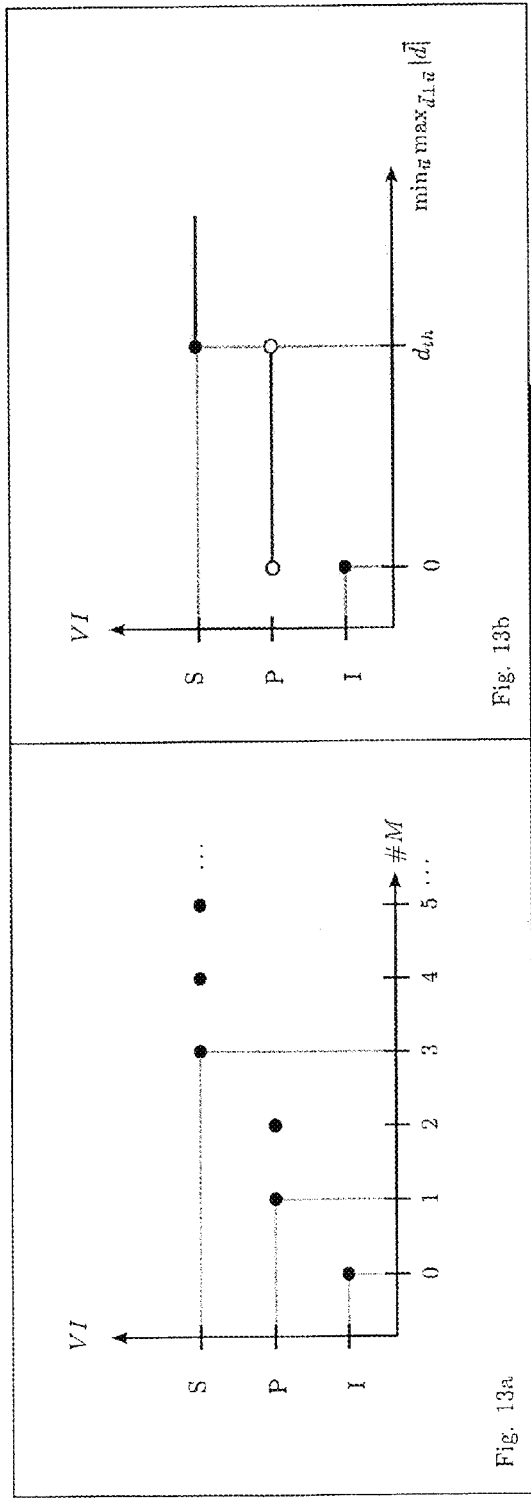
Fig. 13a
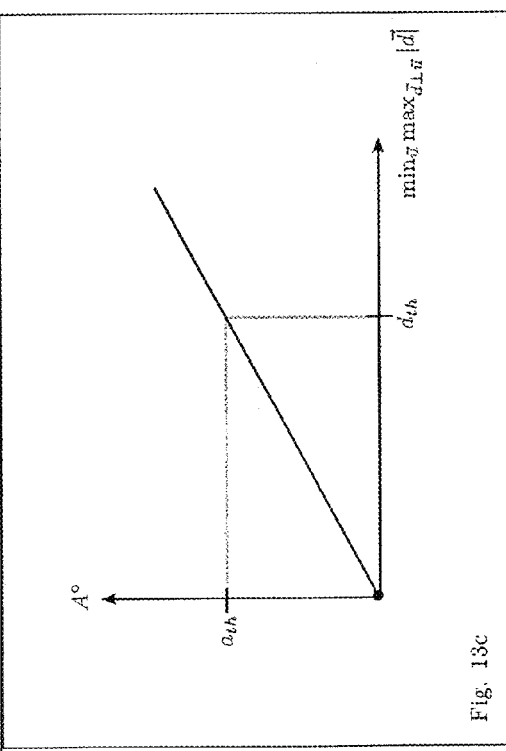
Fig. 13b
Fig. 13c

OPTICAL TRACKING

BACKGROUND OF THE INVENTION

The present invention relates to a method for determining the pose of an object, preferably of a hand-held medical device such as an ultrasound probe.

In various technical fields, it is of great importance to accurately determine the pose, i.e., the three-dimensional orientation and position, of an object while the object is being moved. For example, data acquired during ultrasound imaging may be improved if the pose of the ultrasound probe can be accurately determined during the process of acquiring the data. It has been suggested to determine the pose of such an ultrasound probe by means of optical tracking. For example, US 2004/0100557 A1 discloses a method for tracking the position and orientation of an ultrasound beam emitted from an ultrasound probe using, e.g., a three-dimensional video tracking system. According to this known method, the object to be tracked is provided with specific marker elements which are imaged by the video system. Analyzing the images taken by the video system allows for determining the three-dimensional position and orientation of the ultrasound probe as long as these markers are visible to the system.

However, during the process of imaging a patient by means of ultrasound, the user of the ultrasound device often has to perform complicated movements in order to properly image the patient. During these movements, one or even most of the markers on the ultrasound probe may be covered, e.g., by a hand of the user or the user in another way obstructs the field of view of the two cameras. While the markers are not fully visible to the video tracking system, the full pose information cannot be determined. The ultrasound image data taken during such a period of time may be of worse quality or even useless.

SUMMARY OF THE INVENTION

It is therefore an object of the present invention to provide an improved method for determining the pose of an object, in particular, of an ultrasound probe, which addresses the above discussed problem.

Accordingly, the present invention relates to a method for determining the pose of an object, preferably of a medical device such as an ultrasound probe. According to said method, an object, preferably a medical device such as an ultrasound probe, is provided. The object comprises at least one visual identification element and an orientation sensor for determining an absolute orientation and/or angular velocity of the object. Moreover, at least two cameras are provided which are adapted to visually track the visual identification element, each camera having a field of view and remaining stationary during the method. The cameras define a camera coordinate system.

Image data of the field of view of the at least two cameras are acquired while the object is being moved. Likewise, orientation data provided by the orientation sensor is acquired while the object is being moved. Thus, the method provides for one or more given time intervals or at several time points image data and orientation data. Of course, the object may also rest from time to time. Yet, the inventive method in particular deals with tracking the object during its movement.

The method further comprises calibrating the orientation sensor with respect to the camera coordinate system which allows for comparing the image data with the orientation data in one and the same coordinate system, e.g., the camera coordinate system. The image data and the orientation data are then analyzed to determine the pose of the object during its movement (including possible phases of rest). The pose of the object consists of three-dimensional position data and three-dimensional orientation data. According to the present invention, the position of the object is determined either on the basis of the image data alone or on the basis of a combination of the image data and the orientation data depending on the status of visibility. Similarly, the orientation of the object is determined either on the basis of the orientation data alone or on the basis of the orientation data and/or the image data depending on the visibility of the identification element.

In particular, the orientation of the object is determined on the basis of the orientation data and/or the image data when at least a portion of the visual identification element is sufficiently visible to both cameras to allow for determining the orientation of the object. If, however, not even a portion of the visual identification element is sufficiently visible to both cameras to allow for determining the orientation of the object, i.e. when the visual identification element is not sufficiently visible to both cameras to allow for determining the orientation of the object, the orientation of the object is determined on the basis of the orientation data alone. The missing visual information is thus supplemented or replaced by information gathered by the orientation sensor.

Similarly, the position of the object is determined on the basis of the image data alone when at least a portion of the visual identification element is sufficiently visible to both cameras to allow for determining the position of the object. If, however, at least a portion of the visual identification element is sufficiently visible to both cameras to allow for identifying said portion and for determining the position of said portion, then the position of the object is determined on the basis of a combination of the image data and the orientation data.

Preferably, the method further comprises the step of estimating the accuracy of determining the orientation of the object on the basis of the orientation data alone and of determining the orientation of the object on the basis of the image data alone and using the procedure providing higher accuracy.

Preferably, the position of the object is determined on the basis of an interpolation if, during a first time interval, not even a portion of the visual identification element is sufficiently visible to both cameras to allow for identifying said portion and for determining the position of said portion. The interpolation is preferably based on the position of the object determined immediately before the first time interval and/or the position of the object determined directly after the first time interval. In addition, the interpolation may be based on the velocity and/or acceleration of the object determined immediately before the first time interval and/or the velocity and/or acceleration of the object determined directly after the first time interval.

The method preferably further comprises determining the position and/or orientation of the visual identification element relative to the object and/or determining the orientation of the orientation sensor relative to the object. These calibration data may be measured by "training" the system or these data may be known from the process of manufacturing. Preferably, the visual identification element comprises several sub-elements and/or portions, which can be distinguished from each other and identified by the cameras. In this case, determining the position and/or orientation of the visual identification element relative to the object preferably comprises identifying each of the sub-elements and/or portions and determining the position of each sub-element and/or portion relative to the object.

The visual identification element may comprise one or a combination of: three or more discrete marker elements, two or more bar codes, one or more 2D bar codes, a regular pattern, an irregular pattern, an arbitrary pattern, a geometric shape, the two- or three-dimensional surface of a portion of the object or the entire object, active and/or passive markers, retro-reflective markers, active markers adapted to change their appearance over time in a predetermined periodic or non-periodic manner. If, for example, the visual identification element consists of three discrete spherical markers, determining the position and/or orientation of the visual identification element relative to the object (for the purpose of calibration) preferably comprises identifying each of the spherical markers and determining the position of each spherical marker relative to the object. If, however, the visual identification element consists of a 2D pattern, determining the position and/or orientation of the visual identification element relative to the object preferably comprises identifying portions of the pattern which can be distinguished from each other and identified by the cameras and determining the position of each such portion relative to the object.

Preferably, the orientation sensor comprises a rate gyro and/or a compass.

Preferably, calibrating the orientation sensor with respect to the camera coordinate system comprises i) acquiring image data of the field of view of the at least two cameras at a first time and determining the orientation of the object at said first time on the basis of said image data, ii) acquiring orientation data provided by the orientation sensor at said first time and determining the orientation of the object at said first time on the basis of said orientation data, and iii) calibrating the orientation sensor with respect to the camera coordinate system by relating the orientations of the object determined according to steps i) and ii) to each other. Of course, said calibration should take place during a first time at which at least a portion of the visual identification element is sufficiently visible to both cameras to allow for determining the orientation of the object. If, during a subsequent time interval, the image data do not allow for determining the orientation of the object, said orientation may be derived from the orientation data provided by the orientation sensor.

Preferably, calibrating the orientation sensor with respect to the camera coordinate system is performed at several times during the inventive method, i.e. at several times while the object is being moved. The pose for a given time is then preferably determined on the basis of a calibration of the object which is closest in time to said given time because the quality of the orientation data provided by the orientation sensor decreases over time. In case of a simultaneous tracking usually the last calibration before the current time is used. If the data is saved and tracking is performed afterwards, a calibration which has taken place after a specific time may be used for said specific time.

Preferably, feedback is provided to a user, the feedback comprising one or a combination of the following: indication of a successfully performed calibration according to step e), current accuracy of determining the orientation from the image data, current accuracy of determining the orientation from the orientation data, indication of when a next calibration has to be performed in order to achieve a predefined level of accuracy.

The object preferably is a hand-held medical device, more preferably an ultrasound probe.

Optionally image data of the field of view of the at least two cameras are recorded while the object is being moved. Moreover, orientation data is optionally recorded as well while the object is moved. Finally, the recorded or live image data and the recorded or live orientation data are analyzed to determine the pose of the object during its movement.

As mentioned previously, the method comprises the step of calibrating the means (orientation sensor) for determining an absolute orientation and/or angular velocity of the object. Preferably, the means for determining an absolute orientation and/or angular velocity of the object is, as such, only adapted to measure a relative orientation of the object relative to a certain known or predetermined orientation of the object. In order to ascertain the absolute orientation (in world coordinates) over time it is preferred to at least once determine the absolute orientation, e.g. by using the image data, and to subsequently measure the relative orientation versus said once determined absolute orientation. Preferably, this calibration is performed if the object is in a resting state. If the orientation of the object is once precisely known, the orientation of the object during any subsequent movement can be calculated if, e.g., the angular velocity is determined. Optionally, the object is put into a predetermined resting or calibration state, in which the orientation of the object is known. The means for determining an absolute orientation and/or angular velocity of the object is then calibrated in this resting or calibration state. In addition, or alternatively, a calibration may take place by determining the orientation of the object using the image data during one or more time intervals in which the visual identification element is sufficiently visible to both cameras to allow for determining the orientation of the object. Such additional calibration may also take place during movement of the object, which allows for several recalibrations during a longer interval of moving the object.

The inventive method preferably further comprises the step of determining the position and/or the orientation of the visual identification element relative to the object. In other words, it should preferably be known how the identification element is arranged on or attached to the object in order to be able to determine, e.g., the position of the object on the basis of the image data taken from the visual identification element. The position and/or orientation of the visual identification element relative to the object may be measured or taken, e.g., from the manufacturing specifications.

The gist of the present invention will be explained in the following referring to an object comprising at least one visual identification element which consists of three individual marker elements. However, the present invention is not limited to such an identification element.

Viewing three such distinct markers by means of at least two stereoscopically arranged cameras allows for identifying the three-dimensional position of each of these markers in space. Knowing the position of the markers relative to the object, these marker positions in space allow for calculating both the position of the object and the orientation of the object, i.e., the entire pose information. If, however, one of the markers is not visible to both cameras, the position of said "missing" marker cannot be determined. Yet, knowing the position of only two markers does not allow for determining either the position or the orientation of the object, because the object can rotate around an axis defined by the two markers without affecting the position of these two markers, and the center and/or the origin of the object not necessarily lies on said axis. If, however, the orientation of the object is known by determining an absolute orientation and/or angular velocity of the object during movement, a combination of said orientation data with the image data of the two uniquely identified markers allows for determining the position of the object. This is, in fact, even possible if only a single uniquely identified marker is visible to both cameras as long as the orientation of the object is determined separately. As determining the position of the object on the basis of a combination of the image data and the orientation data requires both the position of at least one of the three markers in three-dimensional space and the position of said marker relative to the object, it is necessary to both identify the marker and determine the position of said marker.

In the case of three distinct markers, the "portion of the visual identification element" sufficient to allow for identifying said portion and for determining the position of said portion would be, e.g., one of these markers. As long as one of these markers is sufficiently visible to both cameras to allow for identifying the marker and for determining the position of the marker, the position of the object can be determined on the basis of the position of said marker (via the image data) in combination with the orientation data provided, e.g., by a rate-gyro.

If however, the three markers, i.e., the entire visual identification element, are sufficiently visible to both cameras to allow for determining the position of the object (using the position of each of these markers), the position of the object can be determined on the basis of the image data alone.

The orientation of the object may be determined on the basis of either the orientation data provided by, e.g., the rate-gyro, or the image data. If the visual identification element, i.e., the three markers in the example, is not sufficiently visible to both cameras to allow for determining the orientation of the object, the orientation of the object is determined on the basis of the orientation data provided by the means for determining an absolute orientation and/or angular velocity of the object. If, on the other hand, the visual identification element is sufficiently visible to both cameras to allow for determining the orientation of the object, the orientation of the object may be determined on the basis of the orientation data only, on the basis of the image data only, or on the basis of a combination of the orientation data and the image data.

The latter is preferably decided on the basis of the estimated accuracy of the different ways of determining the orientation of the object. Preferably, the accuracy of determining the orientation of the object on the basis of the orientation data and of determining the orientation of the object on the basis of the image data is estimated and the data providing higher accuracy is used for determining the orientation of the object. The accuracy of the image data may, e.g., depend on characteristic lengths of the visual identification element which is visible to both cameras or on the distance between the object and the two cameras. The accuracy of the orientation data, on the other hand, may depend on the amount of time which has passed since the last calibration of, e.g., the rate-gyro.

Thus, by using the supplementary information provided by the means for determining an absolute orientation and/or angular velocity of the object, the present invention allows for determining the complete pose information of an object even if the visual identification element is only partially visible, that is only one marker in the above example, is visible. Accordingly, a much more complete and more accurate data set can be provided by the inventive method.

If, during a first time interval, not even a portion of the visual identification element is sufficiently visible to both cameras to allow for identifying said portion and determining the position of said portion, the position of the object is preferably determined on the basis of an interpolation. The interpolation is preferably based on the position of the object determined immediately before the first time interval and/or the position of the object determined directly after the first time interval. For example, the position of the object may be a linear interpolation between those two positions during the first time interval. In addition, the interpolation is preferably based on the velocity of the object determined immediately before the first time interval and/or the velocity of the object determined directly after the first time interval. Alternatively or additionally an accelerometer could be used to interpolate within this time interval based on accelerations.

As mentioned above, the visual identification element need not consist of three distinct marker elements. Rather, the visual identification element can comprise any one or a combination of: three or more discrete marker elements, two or more bar codes, one or more 2D bar codes, a regular pattern, an irregular pattern, an arbitrary pattern, a geometric shape, and the like, or even the two- or three-dimensional surface of a portion of the object or the entire object. The visual identification element may comprise passive markers such as disk-shaped markers on the surface of the object (which may, be retro-reflective) and/or active markers such as, e.g., LEDs which are preferably able to change their appearance over time in a predetermined periodic or non-periodic fashion. If three or more discrete marker elements are used, these three or more discrete marker elements are preferably arranged in an asymmetric manner and preferably distinct from each other in order to allow for uniquely identifying each of these marker elements individually. For example, the discrete marker elements can have different shapes, sizes, colors or additional markings on the marker elements.

In case of some gyro sensors it is preferred to also perform a reset, which has to be done in a resting state. Preferably, the resting state is determined by analyzing the image data. Alternatively, an input may be provided by a user that the object is in the resting state.

Even though the present invention has been described with reference to an ultrasound probe, it is to be emphasized that the present invention may be utilized for determining the pose of any object. Preferably, the present invention may be used for determining the pose of a medical device, preferably a hand-held medical device. The present invention is particularly suited for determining the pose of an ultrasound probe.

The present invention further relates to an ultrasonic device for ultrasonic imaging comprising an ultrasound probe, at least two cameras and a processor. The ultrasound probe comprises at least one visual identification element and an orientation sensor for determining an absolute orientation and/or angular velocity of the ultrasound probe. The processor is adapted to perform the method steps discussed above with reference to the inventive method.

BRIEF DESCRIPTION OF THE DRAWINGS

Preferred embodiments of the present invention will be further elucidated with reference to the following Figures, which show:

FIG. 1 a legend for the following Figures;

FIG. 2 schematically the calibration of the means for determining an absolute orientation and/or angular velocity (gyro) to the object;

FIG. 3 schematically the calibration of the visual identification element to the object;

FIG. 4 schematically the relative rotation of the gyro during a time interval;

FIG. 5 schematically detection of sufficient visual identification element information to determine the pose of the object with optical tracking;

FIGS. 6a and 6b schematically detection of partial visual identification element information with optical tracking;

FIG. 7 schematically calculation of the pose of the object;

FIG. 11 schematically angular accuracy determination as a function of positional accuracy;

FIG. 12 schematically arrangement of four coplanar but non-colinear markers; and FIGS. 13a-c conceptually the difference between sufficient and partial visual identification element information.

DETAILED DESCRIPTION OF THE INVENTION

Figure 8A:
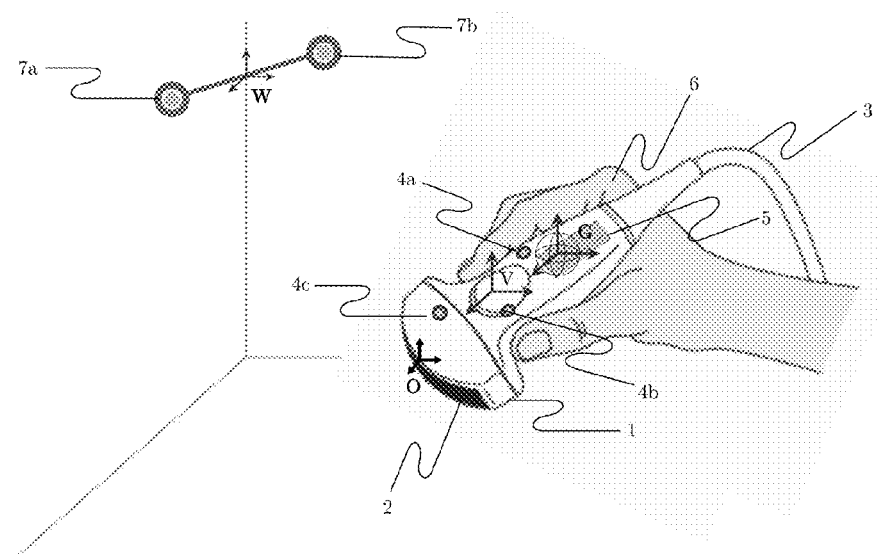
FIGS. 8a and 8b an ultrasound probe.

Parts of the following detailed description specifically refer to a method for determining the pose of an ultrasound probe. However, as mentioned previously, the entire invention, including all preferred features, may generally be utilized in a method for determining the pose of any object.

Optical tracking in general provides high pose accuracy, but suffers from line-of-sight issues (all-or-nothing: complete pose information or no information at all). Rate-gyro sensors provide highly accurate relative orientation information, but only for short periods of time (typically approximately one minute). Three-dimensional optical tracking works by having a stereo camera setup which recognizes or images a visual identification element of known shape and/or size and/or geometry and/or configuration. Image analysis of the camera data along with the known geometry of the visual identification element are used to determine the visual identification element's pose relative to the camera setup. Since the camera setup will remain stationary during any given tracking session, the coordinate system of the camera and the world coordinate system are effectively the same and no distinction will be made between them from here on out. Currently known optical tracking systems deliver pose information when the visual identification element information is sufficiently visible to both cameras, i.e., if the visual identification element is sufficiently visible to both cameras to allow for determining the position of the object. If only partial visual identification element information is available to either one of the cameras, no pose information is delivered. The present invention aims at using this neglected information in conjunction with the relative and/or absolute orientation information delivered from, e.g., the rate-gyro and/or compass to extend the effective usability of the optical tracking system.

The visual information about the visual identification element collected by the cameras can be classified into three categories: sufficient, partial and inadequate. Current state-of-the-art optical tracking systems only deliver pose information when the visualization of the visual identification element is sufficient, i.e., enough information of the visual identification element for pose determination is clearly visible to both cameras. The present invention extends the capability of optical tracking systems to deal with the case when the visual identification element is only partially visible (to either or both cameras) by incorporating the use of a rate-gyro sensor. The case of inadequate visual information occurs, e.g., when the visual identification element is too far away to be identified or usually when no part of it is in the field of the view of both cameras.

When the visualization of the visual identification element is sufficient, the optical tracking system provides the full pose of the object being tracked. When the visualization of the visual identification element is only partial however, it is still possible to determine the position of the partially observed part of the visual identification element, but not the position of the object being tracked. The position of the object being tracked, because its origin is locationally distinct from the detected position in the general case, can no longer be uniquely determined. If one, however, combines this information (position of the partially observed section of the visual identification element) with the orientation of the entire object being tracked, one may recover the full pose of the object being tracked. Preferably, the information from a rate-gyro is used to determine the full pose of the object being tracked, in the absence of sufficient visual information.

Therefore, preferably the transformation between the rate-gyro and the visual identification element and the orientation of the visual identification element at one single point in time during the scan session is determined. The scan session generally relates to the duration of time during which the visual identification element is being tracked. The scan session consists of periods of time when the visualization of the visual identification element is sufficient, and periods of time when the visualization is partial. For the periods of time, when the visualization is partial, full object pose information can be calculated. The periods of time when the visualization of the VTE is partial should preferably be restricted in duration to periods less than or equal to the maximum allowable time depending on the rate-gyro sensor. The minimum required period of time when the visualization of the visual identification element is complete is typically one single video frame of the optical tracking, and this can occur at any time during the scanning session.

Several preferred steps of the inventive method are schematically shown in FIGS. 2 to 7. A legend is provided in FIG. 1 showing translation in terms of a coordinate system (A), rotation between coordinate systems (B), transformation between coordinate systems in terms of complete pose information (C), calculated pose by detected sufficient visual identification element information (D) and calculated pose, when partial visual identification element is available, according to the present invention (E). Generally, a transformation between coordinate systems (C) consists of a translation (A) and a rotation (B).

FIG. 2 schematically shows the calibration of the gyro (G) to the object being tracked (O). FIG. 2 only shows a rotation between coordinate systems (B in FIG. 1) because only the relative orientation is relevant for the gyro-object calibration. During said calibration the constant transformation between the rate-gyro reference frame and the object reference frame is determined. It remains constant throughout the scanning session. Moreover it only needs to be determined once, e.g., when the rate-gyro is mounted onto the object (e.g., the ultrasound probe).

FIG. 3 schematically shows the calibration of the visual identification element (V) and the object being tracked (O). Said calibration comprises both translation and rotation and accordingly, FIG. 3 shows the arrow designating a complete pose transformation (C in FIG. 1). Depending on the type of visual identification element, this process consists of calibrating a position vector to each marker or getting a description of a visual surface pattern in three dimensions by a scan. The visual identification element-object calibration also needs to be performed only once, e.g., when the object is provided with the visual identification element.

The inventive method preferably also comprises a gyro-camera calibration during which the orientation of the rate-gyro sensor in world (camera) coordinates is determined. This should preferably take place at least once during each scan session. The relative rotation of the gyro during a tune interval $[t_i, t_{i+1}]$ may then be measured using the rate-gyro (see FIG. 4).

It is further preferred to re-initialize or reset the rate-gyro settings to compensate for inaccuracies resulting in a constant angular velocity offset. This has to be done in the resting state. Preferably, such a calibration or re-initialization is performed at least once for each scanning session for optimal accuracy.

FIG. 5 schematically shows the detection of sufficient visual identification element information with optical tracking. In the example shown, the visual identification element (V) consists of ten individual marker elements sketched as dots. In this example, sufficient visual identification element information does not require that each of these ten individual marker elements is visible to both cameras. Rather, it may be sufficient if three of these marker elements are visible to both cameras to allow for determining the pose of the visual identification element and, accordingly, the position of the object.

FIGS. 6a and 6b schematically shows the detection of partial visual identification element information with tracking. In FIG. 6a, one of the ten individual marker elements of the visual identification element (V) is sufficiently visible to both cameras to allow for determining the position of this single marker element, i.e., of this portion of the visual identification element (V). However, the transformation between the object (O) and the world coordinate system (W) is still ambiguous because any orientation of the object (O) around that single marker element would, in general, be possible. Yet, if in addition the orientation of the object (O) is known from the rate-gyro, the full pose can be uniquely determined as shown in FIG. 6b.

FIG. 7 schematically shows a preferred embodiment of the method for determining the pose of an object according to the present invention. At the time $t_0$ sufficient visual identification element information is available allowing the determination of the full pose of the object in world coordinates on the basis of the image data provided by the at least two cameras. The rate-gyro provides relative rotations between $t_0$ and $t_1$ as well as between $t_1$ and $t_2$. In combination with the known pose of the object in world coordinates at $t_0$ (and the calibration of the object to the gyro) full orientation information of the object in relation to world coordinates at $t_1$ and $t_2$ can be calculated. At the time $t_2$ only partial visual identification element information is available. In other words, the visual identification element is not sufficiently visible to both cameras to allow the determination of the position of the object, while at least a portion of the visual identification element (here: a single marker) is sufficiently visible to both cameras to allow the identification of said portion and for determining the position of said portion. As discussed above with reference to FIGS. 6a and 6b, said information in combination with the orientation information in world coordinates from the rate-gyro, allows for achieving full pose information at the time $t_2$. Additionally the full pose of the object can be determined at time $t_1$ by using the rate-gyro information to determine the object's orientation and using the already determined positions at times $t_0$ and $t_2$ to interpolate the object's position.

Figure 8B:
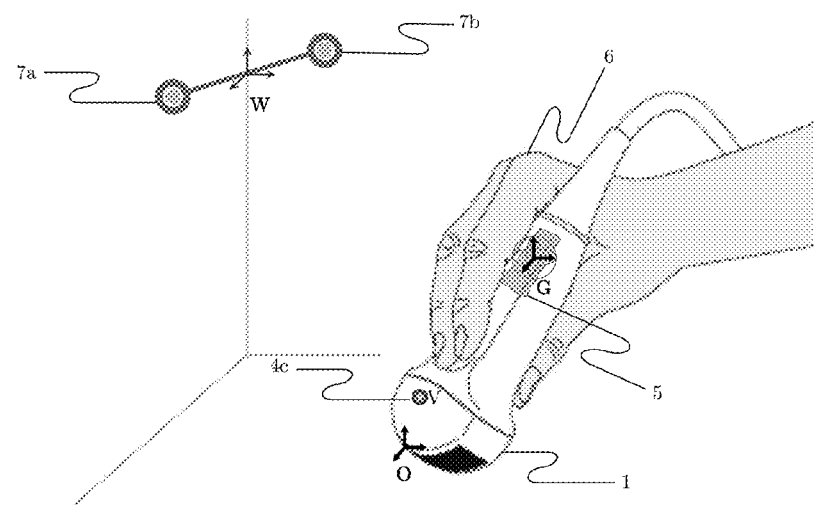

As discussed previously, the method according to the present invention may be used for determining the pose of an ultrasound probe 1 as shown in FIGS. 8a and 8b. The ultrasound probe 1 comprises a transducer array 2 and may be connected to an ultrasound device via a cable 3. The ultrasound probe 1 further comprises a visual identification element 4 consisting, in the shown embodiment, of three discrete marker elements 4a, 4b and 4c. Even though these separate marker elements 4a, 4b and 4c are schematically shown as being identical in FIG. 8a, it is preferred that these marker elements are distinct from each other by means of shape, size, color or the like in order to enable the two cameras 7a and 7b to identify each of the marker elements 4a, 4b and 4c. The ultrasound probe 1 further comprises a rate-gyro sensor 5 for determining the angular velocity of the ultrasound probe 1.

In the situation shown in FIG. 8a, the entire visual identification element 4, i.e., all three individual marker elements 4a, 4b and 4c, are sufficiently visible to the two cameras 7a and 7b to allow the determination of the position of the object by means of the image data provided by the two cameras. However, if the marker elements 4a and 4b are, e.g., covered by a hand 6 of a user as shown in FIG. 8b, only a single marker element 4c, i.e., a portion of the visual identification element 4, may be sufficiently visible to both cameras to allow for identifying said individual marker element 4c and for determining the position of said marker element 4c. The full pose information may then be determined as discussed above on the basis of a combination of the image data provided by the two cameras 7a and 7b and the output of the rate-gyro sensor 5.

Figure 9:
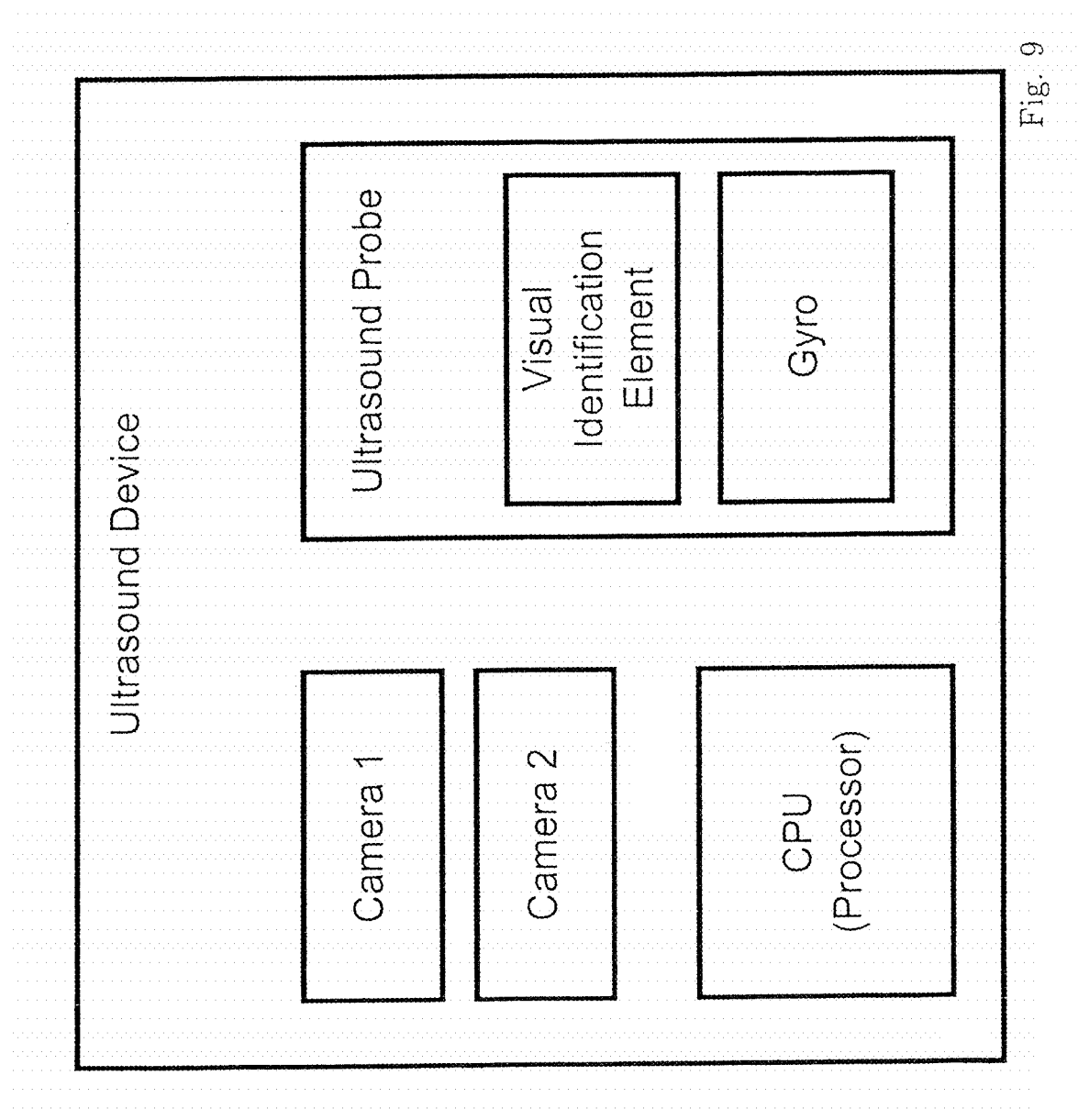
FIG. 9 a block diagram of an ultrasound device.

FIG. 9 shows a block diagram of an ultrasound device according to the present invention. The ultrasound device for ultrasonic imaging comprises an ultrasound probe, at least two cameras and a CPU or a processor. The ultrasound probe comprises at least one visual identification element and means for determining an absolute orientation and/or angular velocity of the ultrasound probe such as a gyro. The processor or central processing unit is adapted to perform the method according to the present invention as described above.

Figure 10A:
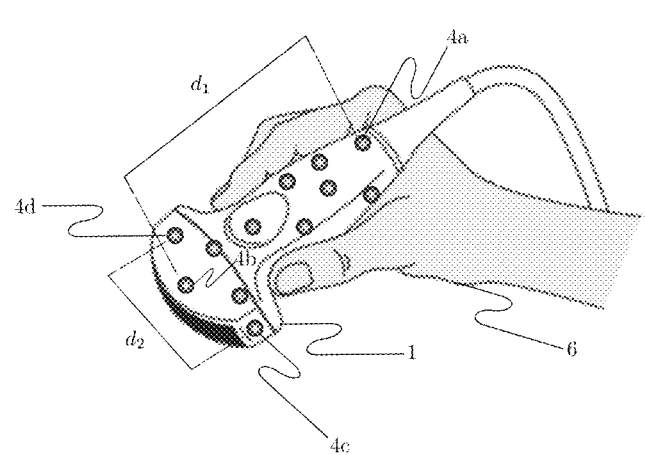
FIGS. 10a and 10b ultrasound probes with different visual identification elements.
Figure 10B:
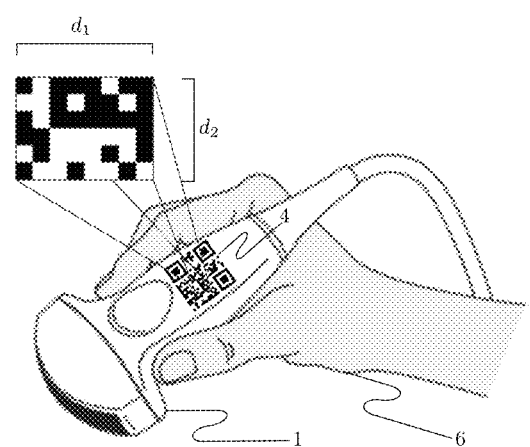

FIGS. 10a and 10b each shows an ultrasound probe 1 with alternative visual identification elements 4. In the embodiment shown in FIG. 10a, the visual identification element comprises several individual, discrete marker elements, whereas the visual identification element of the embodiment shown in FIG. 10b consists of a 2D bar code. The angular accuracy for determining the orientation of the ultrasound probe 1 depends on the characteristic distances of the portion of the visual identification element visible to the two cameras. If discrete markers are being used as shown in FIG. 10a, the characteristic distance in a given direction is determined by the maximum projected distance between any two of the visible markers. For example, in the situation shown in FIG. 10a, the characteristic distance $d_1$ along a first axis is defined by the distance between the two markers 4a and 4b, whereas the characteristic distance $d_2$ along a second perpendicular axis is defined by the distance between the two markers 4c and 4d. If a continuous plane pattern is being used as shown in FIG. 10b, the characteristic distances are the longest projected distances for each angle of the recognizable portion of the pattern, e.g. $d_1$ along a first axis and $d_2$ along a second perpendicular axis in case the enlarged portion of the pattern shown in FIG. 10b is visible to the cameras.

In any case, the angular accuracy increases as the characteristic distance increases. FIG. 11 illustrates the relationship between the characteristic distance, the positional error and angular error. If d represents the characteristic distance and $\delta x \ll d$ represents the positional error, then the maximum angular error $\delta\theta$ is given by $\tan(\delta\theta)=2\delta x/d$. For characteristic distances significantly larger than the positional error, $\tan(\delta\theta)=\delta\theta$ using the small angle approximation, thus the angular error decreases as d increases, or in other words the rotational accuracy increases as d increases. The rotational accuracy determined by the characteristic distance d applies to rotations whose axes lie in the plane perpendicular to d. In FIG. 11 the plane is denoted by P and the axis of rotation is denoted by $\vec{u}$. Each of $d_1$ and $d_2$ define the rotational accuracy in the two dimensions perpendicular to the $d_1$ axis and the $d_2$ axis, respectively. Accordingly, a visual identification element as shown in FIGS. 10a and 10b on a single plane with two large perpendicular characteristic distances $d_1$ and $d_2$ on this plane is sufficient for accurate determination of the orientation in three dimensions. FIG. 12 shows our coplanar but non-colinear markers with characteristic distances $d_1$ and $d_2$. The total angular accuracy in three dimensions may be given by the minimum angular accuracy achievable in any one dimension, including the ones distinct from the $d_1$ axis and the $d_2$ axis. The depicted axis of rotation $\vec{u}$ is the one about which the angular accuracy is the least. In general according to the accuracy definition the angular accuracy about an arbitrary axis of rotation in three dimensions is approximately proportional to the maximum achievable distance between the axis and, e.g., one of the discrete optical markers. If $A°_{\vec{u}}$ represents the if angular accuracy about the axis $\vec{u}$, then $A°_{\vec{u}} \sim \max_{\vec{d} \perp \vec{u}} |\vec{d}|$. If $A°$ represents the total angular accuracy in three dimensional space, then $A°=\min_{\vec{u}} A°_{\vec{u}}$.

With continuous patterns, one has continuous loss or gain of accuracy with decreasing or increasing characteristic distance. If one uses spherical markers, accuracy also depends on distance, but it is not continuous with covering (they go on and off), yet of course continuous with perspective. With a continuous pattern, the difference between sufficient and partial visual identification element information can be defined by a threshold for minimum acceptable rotational accuracy. This concept is illustrated in FIG. 13. FIG. 13a depicts the classification of the amount of visual identification element information (VI) into the three categories sufficient (S), partial (P), and inadequate (I) for the case of discrete markers. The number of discrete markers visible to the camera (#M) determine the amount of information. Three or more non-colinear markers correspond to the state of sufficient information to determine the full pose. One or two markers correspond to the state of partial information where the position of the visible portion can be determined, but not the complete orientation. Zero markers visible correspond to the state of inadequate information to determine any pose data. FIG. 13b depicts the relationship between the two characteristic directions $d_1$ and $d_2$, and the total angular accuracy $A°$ in all three spatial directions. A threshold accuracy $a_{th}$ is determined and is directly related to the minimum characteristic distance threshold $d_{th}$. This threshold accuracy determines the transition in state from partial to sufficient visual identification element information in the case of a 2D pattern, as depicted in FIG. 13c. The cutoff between partial and inadequate visual identification element information in the case of a 2D pattern occurs when the pattern is no longer visible or distinguishable to both cameras and the accuracy goes to zero.

According to a preferred embodiment, the weight of using rotation data provided by, e.g., the rate-gyro sensor and image data (optical tracking), can be shifted continuously depending on the accuracy. Alternatively, cutoff points for accuracy may be provided. Either of these preferred embodiments may be combined with determining the accuracy of the rate-gyro sensor in dependence on its drift rate and the desired orientation and accuracy. Moreover, it is preferred that the rotational dimensions with their differing accuracies (see above) are treated independently.

As discussed previously, sufficient visual identification element information does not necessarily require that the whole visual identification element is visible to both cameras. Rather, the visible portion of the visual identification element needs to be sufficient for determining the full pose with acceptable accuracy. If spherical or disc markers are being used, at least three uniquely identified markers are required for sufficient visual identification element information. If a QR-code or a random or structured pattern is being used, a portion of the code or pattern of minimum size for rotational accuracy is necessary for sufficient visual identification element information. Partial visual identification element information, on the other hand, may refer to one or more uniquely identified spherical or disc markers or an identifiable portion of a code or pattern. Inadequate visual identification element information corresponds to no markers being visible or to the markers being so far away that all markers excite the same element of, e.g., the CCD array, making it impossible to distinguish among them.

The visual identification elements of the present invention can be active (e.g., infrared diodes) or passive (e.g., retro-reflective). They can be individual markers or be patterned. They can have specific shapes (disc, sphere and the like), or be the appearance of the tracked object itself.

In the case that only a portion of the visual identification element is visible to the cameras providing partial tracking information, i.e., providing the position of the visible portion but neither the position nor orientation of the visual identification element itself, the position and orientation of the object being tracked can be determined, for example, as follows.

Let $p_1$ represent the position vector of the portion of the visual identification element visible to the cameras in world or camera coordinates (W), and $p_2$ represent the position vector of the portion of the visual identification element visible to the cameras in visual identification element coordinates (V). Note that $p_1$ changes as the object moves, but that $p_2$ is constant since the visual identification element itself is rigid and any portion of it remains at a constant position and orientation relative to its own coordinate system, i.e., the coordinate system determined by the visual identification element. The rigid transformation between the visual identification element coordinate system and the object coordinate system (O) depicted in FIG. 3 is determined by the visual-identification-element-to-object calibration procedure and is performed preferably at the point in time when the visual identification element is firmly attached to the object. This rigid transformation represents the pose of the object coordinate system relative to the visual identification element coordinate system, $$_OT^V = (_OR^V, p_{OV})$$

where $p_{OV}$ is the translation from object coordinate system to the visual identification coordinate system and $_OR^V$ is the rotation matrix that converts position vectors in visual identification element coordinates to object coordinates. This pose information can be used to determine $p_3$ the position of the portion of the visible identification element visible to the cameras in object coordinates:

$$p_3 = p_{OV} + {}_OR^V \cdot p_2.$$

In FIG. 6a $p_1$ is represented by the arrow from the origin of the world coordinate system (W) to the black dot representing the portion of the visual identification element visible to the cameras, and $p_3$ is represented by the arrow from the origin of the object coordinate system (O) to the black dot representing the portion of the visual identification element visible to the cameras.

In order to determine the position of the object in world coordinates $p_{WO}$, we need the rotation matrix ${}_WR^O$ which converts position vectors in object coordinates to position vectors in world coordinates. Then we would have $$p_{WO} = p_1 + {}_WR^O \cdot p_3.$$

But the rotation matrix ${}_WR^O$ is exactly the orientation of the object in world coordinates, and this we have from the orientation ${}_WR^O$ of the gyro sensor (G) in world coordinates and the pre-determined relative orientation between the gyro sensor and the object ${}_GR^O$, depicted in FIG. 2. That is, $${}_WR^O = {}_WR^G \cdot {}_GR^O.$$

Thus we have the complete pose of the object in world coordinates $${}_WT^O = ({}_WR^O, p_{WO}).$$

The invention claimed is:

1. Method for determining the pose of an object the method comprising the following steps:
   a) providing an object comprising at least one visual identification element and an orientation sensor for determining an absolute orientation and/or angular velocity of the object;
   b) providing at least two cameras adapted to visually track the at least one visual identification element, each camera having a field of view and remaining stationary during the method, the cameras defining a camera coordinate system;
   c) acquiring image data of the field of view of the at least two cameras while the object is being moved;
   d) acquiring orientation data provided by the orientation sensor while the object is being moved;
   e) calibrating the orientation sensor with respect to the camera coordinate system; and
   f) analyzing the image data and the orientation data to determine the pose of the object during its movement; wherein:
      f1) the orientation of the object is determined on the basis of the orientation data and/or the image data when at least a portion of the visual identification element is sufficiently visible to both cameras to allow for determining the orientation of the object;
      f2) the orientation of the object is determined on the basis of the orientation data alone when the visual identification element is not sufficiently visible to both cameras to allow for determining the orientation of the object;
      f3) the position of the object is determined on the basis of the image data alone when at least a portion of the visual identification element is sufficiently visible to both cameras to allow for determining the position of the object; and
      f4) the position of the object is determined on the basis of a combination of the image data and the orientation data determined according to step f1) or f2) when at least a portion of the visual identification element is sufficiently visible to both cameras to allow for identifying said portion and for determining the position of said portion.

2. The method according to claim 1, wherein step f1) further comprises the step of estimating accuracy of determining the orientation of the object on the basis of the orientation data alone and of determining the orientation of the object on the basis of the image data alone and using the procedure providing higher accuracy in step f1).

3. The method according to claim 1, wherein the position of the object is determined on the basis of an interpolation if, during a first time interval, not even a portion of the visual identification element is sufficiently visible to both cameras to allow for identifying said portion and for determining the position of said portion.

4. The method according to claim 3, wherein the interpolation is based on the position of the object determined immediately before the first time interval and/or the position of the object determined directly after the first time interval.

5. The method according to claim 3, wherein the interpolation is based on the velocity and/or acceleration of the object determined immediately before the first time interval and/or the velocity and/or acceleration of the object determined directly after the first time interval.

6. The method according to claim 1, further comprising determining the position and/or orientation of the visual identification element relative to the object and/or determining the orientation of the orientation sensor relative to the object.

7. The method according to claim 6, wherein the visual identification element comprises several sub-elements and/or portions, which can be distinguished from each other and identified by the cameras, and wherein determining the position and/or orientation of the visual identification element relative to the object comprises identifying each of the sub-elements and/or portions and determining the position of each sub-element and/or portion relative to the object.

8. The method according to claim 1, wherein the visual identification element comprise one or a combination of: three or more discrete marker elements, two or more bar codes, one or more 2D bar codes, a regular pattern, an irregular pattern, an arbitrary pattern, a geometric shape, the two- or three-dimensional surface of a portion of the object or the entire object, active and/or passive markers, retro-reflective markers, active markers adapted to change their appearance over time in a predetermined periodic or non-periodic manner.

9. The method according to claim 1, wherein the orientation sensor comprises a rate gyro and/or a compass.

10. The method according to claim 1, wherein calibrating the orientation sensor with respect to the camera coordinate system comprises i) acquiring image data of the field of view of the at least two cameras at a first time and determining the orientation of the object at said first time on the basis of said image data, ii) acquiring orientation data provided by the orientation sensor at said first time and determining the orientation of the object at said first time on the basis of said orientation data, and iii) calibrating the orientation sensor with respect to the camera coordinate system by relating the orientations of the object determined according to steps i) and ii) to each other.

11. The method according to claim 1, wherein calibrating the orientation sensor with respect to the camera coordinate system is performed at several times, while the object is being moved and wherein the pose for a given time is determined on the basis of a calibration of the object which is closest in time to said given time.

12. The method according to claim 1, wherein feedback is provided to a user, the feedback comprising one or a combination of the following: indication of a successfully performed calibration according to step e), current accuracy of determining the orientation from the image data, current accuracy of determining the orientation from the orientation data, indication of when a next calibration has to be performed in order to achieve a predefined level of accuracy.

13. The method according to claim 1, wherein the object is a hand-held medical device.

14. Ultrasonic device for ultrasonic imaging comprising an ultrasound probe, at least two cameras and a processor, wherein the ultrasound probe comprises at least one visual identification element and an orientation sensor for determining an absolute orientation and/or angular velocity of the ultrasound probe and wherein the processor is adapted to perform method steps c) to f) of claim 1.

15. The ultrasonic device according to claim 14, wherein the visual identification element comprise one or a combination of: three or more discrete marker elements, two or more bar codes, one or more 2D bar codes, a regular pattern, an irregular pattern, an arbitrary pattern, a geometric shape, the two or three-dimensional surface of a portion of the object or the entire object, active and/or passive markers, retro-reflective markers, active markers adapted to change their appearance over time in a predetermined periodic or non-periodic manner.

16. The method according to claim 13, wherein the hand-held medical device is an ultrasound probe.

* * * * *